(12) United States Patent
Wang

(10) Patent No.: US 7,387,798 B2
(45) Date of Patent: Jun. 17, 2008

(54) METHOD AND COMPOSITION FOR RESUSCITATION

(76) Inventor: Yanming Wang, 203 Summer St., Malden, MA (US) 02148

( * ) Notice: Subject to any disclaimer, the term of this patent is extended or adjusted under 35 U.S.C. 154(b) by 383 days.

(21) Appl. No.: 11/234,906

(22) Filed: Sep. 26, 2005

(65) Prior Publication Data

US 2006/0128798 A1    Jun. 15, 2006

Related U.S. Application Data

(63) Continuation of application No. 11/013,167, filed on Dec. 15, 2004, and a continuation of application No. 11/193,181, filed on Jul. 28, 2005.

(51) Int. Cl.
*A61K 33/42*  (2006.01)
*A61K 38/00*  (2006.01)
*A61K 31/70*  (2006.01)
*A61K 31/41*  (2006.01)
*A61K 31/34*  (2006.01)

(52) U.S. Cl. ............................. 424/602; 514/2; 514/3; 514/47; 514/363; 514/471

(58) Field of Classification Search .................... None
See application file for complete search history.

(56) References Cited

U.S. PATENT DOCUMENTS

| | | | |
|---|---|---|---|
| 4,378,797 A | 4/1983 | Osterholm | |
| 4,393,863 A | 7/1983 | Osterholm | |
| 4,446,154 A | 5/1984 | Osterholm | |
| 4,788,180 A * | 11/1988 | Bloch .......................... | 514/26 |
| 4,981,691 A | 1/1991 | Osterholm | |
| 5,571,840 A * | 11/1996 | Mayor et al. ............... | 514/567 |
| 6,369,114 B1 * | 4/2002 | Weil et al. .................. | 514/653 |
| 6,500,809 B1 | 12/2002 | Frazer | |
| 6,677,356 B1 * | 1/2004 | Sethi et al. ................. | 514/321 |

OTHER PUBLICATIONS

De Keyser J. Sulter G. Luiten PG. Clinical trials with neuroprotective drugs in acute ischaemic stroke: are we doing the right thing? Trends Neurosci. 1999; 22(12):535-540.
Ames A, Wright RL, Kowada M, Thurston JM, Majno G. Cerebral ischemia: II. The no-reflow phenomenon. Am. J. Pathol. 1968; 52(2):437-453.
Fischer M, Hossmann KA. No-reflow after cardiac arrest. Intensive Care Med. 1995; 21(2):132-141.
Bottiger BW, Krumnikl JJ, Gass P, Schmitz B, Motsch J, Martin E. The cerebral "no-flow" phenomenon after cardiac arrest in rats. Influence of low-flow reperfusion. Resuscitation, 1997; 34(1):79-87.
Follis F, Miller K, Seremin OU, Pett S, Kessler R, Temes T, Wernly JA. Experimental delayed postichemic spinal chord hypoperfusion after aortic cross-clamping. Can. J. Neurol Sci. 22 (1995) 202-207.
Guyton AC. Hall JE. Textbook of Medical Physiology, ninth edition, Chapter 16. WB Saunders company, date not available.

Rosenberg GA, Kyner WT, Estrada E. Bulk flow of brain interstitial fluid under normal and hyperosmolar conditions. Am J Physiol. 1980; 238:42-49.
Milhorat TH, Hammock MK, Fenstermacher JD, Levin VA. Cerebrospinal fluid production by the choroids plexus and brain. Science 1971; 173: 330-332.
Abbott NJ. Evidence for bulk flow of brain interstitial fluid: significance for physiology and pathology. Neurochemistry international. 2004; 45:545-5452.
Voll CL, Auer RN. Insulin attenuates ischemic brain damage independent of its hypoglycemic effect. J Cereb Blood Flow Metab. 1991; 11: 1006-1014.
LeMay DR, Lin G, Zelenock GB, D'Alecy LG. Insulin adminstration protects neurologic function in cerebral ischemia in rats. Stroke. 1988; 19:1411-1419.
Fukuoka S, Yeh HS, Mandybur TI, Tew HM. Effect of insulin on acute experimental cerebral ischemia in gerbils. Stroke. 1989; 20:396-399.
Ono T. Steffens AB. Sasaki K. Influence of peripheral and intracerebroventricular glucose and insulin infusions on peripheral and cerebrospinal fluid glucose and insulin levels. Physiology & Behavior. 1983. 30:301-306.
Krueger RC, Santore MT, Dawson G, Schwartz NB. Increased extracellular magnesium modulates proliferation in fetal neural cell in culture. Developmental brain research. 2001; 127:99-109.
Chaudry IH, Stephan RN, Dean RE, Clemens MG. Use of magnesium-ATP following liver ischemia. Magnesium. 1988; 7:68-77.
Vink R. Magnesium and brain trauma. Magnes Trace Elem. 1991-1992; 10:1-10.
Harkness RA, Coade SB, Webster DB. ATP, ADP and AMP in plasma from peripheral venous blood. Clinica Chimica Acta 1984; 143-91-98.
Muñoz DJB, Thorne PR, Housley GD, Billett TE. Adenosine 5'-triphosphate (ATP) concentrations in the endolymph and perilymph of the guinea-pig cochlea. Hearing Research. 1995; 90:119-125.
Sakama R, Hiruma H, Kawakami T. Effects of extracellular ATP on axonal transport in cultured mouse dorsal root ganglion neurons. Neuroscience. 2003; 121:531-535.
Miyamoto K, et al. A new and simple method of preventing spinal cord damage following temporary occlusion of the thoracic aorta by draining the cerebrospinal fluid. J cardiovasc surg. 1960; 16: 188-97.
Juvonen T. Biancari F, Rimpilainen J, Satta J, Rainio P, Kiviluoma K. Strategies for spinal cord protection during descending thoracic and thoracoabdominal aortic surgery: Up-to-date experimental and clinical results—a review. Scand Cardiovasc J 2002; 36(3):136-60.
Tsusaki B, Grigore A, Cooley DA, Collard CD. Reversal of delayed paraplegia with cerebrospinal fluid drainage after thoracoabdominal aneurysm repair. [Letter] Anesthesia & Analgesia. 94(6):1674, 2002.

(Continued)

*Primary Examiner*—Raymond J. Henley, III

(57) ABSTRACT

The key obstacle for current resuscitation is the acutely limited time window. The major reason for the limited time window is that the brain and spinal cord are extremely vulnerable to hypoxic-ischemic insult. A method and a lymph-like fluid composition for resuscitation of cardiac arrest are provided. The method includes steps of inhibiting CSF production, removing CSF, replacing the CSF with invented lymph-like fluid composition plus conventional CPR. The lymph-like fluid composition includes polypeptides, insulin, elevated magnesium concentration and ATP in artificial CSF.

18 Claims, No Drawings

OTHER PUBLICATIONS

Ortiz-Gomez JR, Gonzalez-Solis FJ. Fernandez-Alonso L. Bilbao JI. Reversal of acute paraplegia with cerebrospinal fluid drainage after endovascular thoracic aortic aneurysm repair. Anesthesiology. 95(5):1288-9, 2001.

Heller LB, Chaney MA. Paraplegia immediately following removal of a cerebrospinal fluid drainage catheter in a patient after thoracoabdominal aortic aneurysm surgery. Anesthesiology. 95(5):1285-7, 2001.

Azizzadeh A. Huynh TT. Miller CC 3rd. Safi HJ. Reversal of twice-delayed neurologic deficits with cerebrospinal fluid drainage after thoracoabdominal aneurysm repair: a case report and plea for a national database collection. Journal of Vascular Surgery. 31(3):592-8, 2000.

Crawford ES, Svensson LG, Hess KR, Shenaq SS, Coselli JS. A prospective randomized study of cerebrospinal fluid drainage to prevent paraplegia after high-risk surgery on the thoracoabdominal aorta. J Vasc Surg. 1991; 13(1):36-45; discussion 45-46.

Granger DN, Gabel JC, Drke RE, Taylor AE.: Physiologic basis for the clinical use of albumin solutions. *Surg Gynecol Obstet*. 1978, 146:97-104.

Lewis RT: Albumin: role and discriminative use in surgery. *Can J Surg*. 1980, 23: 322-328.

Ratzmann KP, Hampel R. Glucose and insulin concentration patterns in cerebrospinal fluid following intravenous glucose injection in humans. Endokrinologie. 1980. 76: 185-188.

Gordon JL. Extracellular ATP: effects, sources and fate. Biochem J. 1986 233: 309-319.

Apostolou E. Deckert K, Puy R. Sandrini A. Leon MPD. Douglass JA Rolland JM, O'Hehir RE. Anaphylaxis to Gelofusine confirmed by in vitro basophil activation test: a case series. Anaesthesia 2006. 61: 264-268.

Craig RL, Poole GV. Resuscitation in uncontrolled Hemorrhage. American Surgeon 1994. 60: 59-60.

Strecker U, Dick W. Madjidi A, Ant M. The effect of the type of colloid on the efficacy of hypertonic saline colloid mixtures in hemorrhagic shock: dextran versus hydroxyethyl starch. Resuscitation 1993. 25: 41-57.

Bickell WH, Bruttig SP, Millnamow GA, O'Benar J, Wade CE. Use of hypertonic saline/dextran versus lactated Ringer's solution as a resuscitation fluid after uncontrolled aortic hemorrhage in anesthetized swine. Annals of emergency medicine. 1992. 21: 1077-1058.

Cullen MJ, Singer M. Severe anaphylactoid reaction to hydroxyethyl starch. Anaesthesia. 1990. 45: 1041-1042.

Dubick MA, Wade CE, HSD development group. Evaluation of the local irritation potential of hypertonic Saline-Dextran (HSD) in mice and rabbits. Journal of applied toxicology. 2004. 24: 409-413.

Lena N. Resuscitation following trauma and hemorrhagic shock: Is hydroxyethyl starch safe? Critical Care Medicine. 1995. 23: 795-797.

Zinderman CE, Landow L, Wise RP. Anaphylactoid reactions to Dextran 40 and 70: Reports to the United states Food and Drug adminstration, 1969 to 2004. J Vasc Surg. 2006. 43: 1004-1009.

Weidhase R, Faude K, Weidhase R. Hydroxyethyl starch—an interim report.Anaesthesiol Reanim. 1998. 23: 4-14.

Widmann MD, Delucia A, Sharp J, Richenbacher WE. Reversal of renal failure and paraplegia after thoracoabdominal aneurysm repair. Ann Thorac Surg. 1998. 65: 1153-1155.

McCullough JL, Hollier LH, Nugent M. Paraplegia after thoracic aortic occlusion influence of cerebrospinal fluid drainage. J Vasc Surg. 1988, 7: 153-160.

Westermaier TH, Hungerhuber E, Zausinger st, Baethmann A, Schmid-Elsaesser R. Neuroprotective efficacy of intra-arterial and intravenous magnesium sulfate in a rat model of transient focal cerebral ischemia. Acta Neurochir. 2003. 145:393-399.

Chaudry IH. Cellular mechanisms in shock and ischemia and their correction. Am J Physiol. 1983. 245: R117-R134.

Rainey TG, Read CA. Pharmacology of colloids and crystalloids. Chapter 15. The pharmacologic approach to the critically ill patent. 3$^{rd}$ edition. Baltimore. Williams and Wilkins 1994. 272-290.

Yenari MA. Heat shock proteins and neuroprotection. Adv Exp Med Biol. 2002. 513:281-299.

Milhorat TH. Choroid Plexus and Cerebrospinal fluid production. *Science*. 1969; 166: 1514-1516.

Uchida K et al. Possible harmful effects on central nervous system cells in the use of physiological saline as an irrigant during neurosurgical procedures. *Surg Neurol* 2004, 62: 96-105.

Mikami C. Suzuki M, Tsuiki K. Ogawa A. Effect of nicardipine and magnesium on cerebral infarction-Brain surface perfusion technique. Cerebrovascular Diseases. 2001. 11:44-50.

Regan RF. Guo Y. Magnesium deprivation decreases cellular reduced glutathione and causes oxidative neuronal death in murine cortical cultures. Brain Research. 2001. 890:177-183.

Muir KW. Lees KR. A randomized, Double-Blind, Placebo-controlled pilot trial of intravenous magnesium sulfate in acute stroke. Stroke. 1995. 26:1183-1188.

Hirasawa H. Chaudry IH, Naue AE. Improved hepatic function and survival with adenosine triphosphate-magnesium chloride after hepatic ischemia. Surgery. 1978. 83:655-662.

Vornov JJ, Thomas AG, Jo D. Protective effects of extracellular acidosis and blockade of sodium/hydrogen ion exchange during recovery from metabolic inhibition in neuronal tissue culture. J Neurochem. 1996. 67:2379-2389.

Wang YF, Gwathmey JK, Zhang G, Soriano SG, He S, Wang Y. Cerebrospinal fluid may mediate CNS ischemic injury. Cerebrospinal Fluid Research. 2005 2:7.

McCarthy KD. Reed DJ. The effect of acetazolamide and furosemide on cerebrospinal fluid production and choroids plexus carbonic anhhydrase activity. J Pharmacol Exp Ther. 1974. 189:194-201.

Lorenzo AV. Greene CS, Hornig GW. Zavala LM. Welch K. The effect of furosemide on intracranial pressure and hemorrhage in preterm rabbits. J Neurosurg. 1989. 70:785-792.

Cottrell JE. Marlin AE. Furosemide and human head injury. The Journal of Trauma. 1981. 21:805-806.

Melby JM. Miner LC. Reed DJ. Effect of acctazolamide and furosemide on the production and composition of cerebrospinal fluid from the cat choroids plexus. Can J Physiol Pharmacol. 1982. 60: 405-409.

Plangger C. Völkl H. Effect of furosemide, bumetanide and mannitol on intracranial pressure in experimental brain edema of the rat. Zent. B1. Neurochir. 1989. 50:142-144.

Greene CS. Lorenzo AV. Hornig G. Kelch K. The lowering of cerebral spinal fluid and brain interstitial pressure of preterm and term rabbits by furosemide. Z Kinderchir. 1985. 40:Supplement I: 5-8.

Magnaes B. Movement of cerebrospinal fluid within the craniospinal space when sitting up and lying down. Surg Neurol. 1978. 10:45-49.

Carlson GD. Oliff HS. Gorden C. Smith J. Anderson PA. Cerebral spinal fluid pressure. Effect of body position and lumbar subarachoid drainage in a canine model. Spine. 2003. 28:119-122.

Barron ME, Wilkes MM, Navickis RJ. A systematic review of the comparative safety of colloids. Arch Surg 2004. 139: 552-563.

Salmon JB, Mythen MG. Pharmacology and physiology of Colloids. Blood Reviews. 1993. 7: 114-120.

Belayev L, Saul I, Huh PW, Finotti N, Zhao W, Busto R, Ginsberg MD. Brain Research 1999, 845: 107-111.

Kass IS, Lipton P. Protection of hippocampal slices from young rats against anoxic transmission damage is due to better maintenance of ATP. Journal of Physiology. 1989. 413: 1-11.

\* cited by examiner

METHOD AND COMPOSITION FOR RESUSCITATION

This is a continuation of the patent application filed Dec. 15, 2004, application Ser. No. 11/013,167; and the patent application filed Jul. 28, 2005, application Ser. No. 11/193,181.

BACKGROUND OF THE INVENTION

1. Field of the Invention

This invention is related to a lymph-like fluid composition and a method of using the composition to protect the brain and spinal cord during resuscitation of cardiac arrest.

2. Background Information

It is estimated that more than 350,000 Americans died of sudden cardiac arrest each year, more than 95 percent of victims die before reaching the hospital. Economic costs for trauma related arrest is over 400 billion dollars each year. Despite numerous scientific advances throughout modern medicine, outcome of resuscitation for arrest victims remains poor. The cardiopulmonary resuscitation (CPR) practice including ventilation, closed chest compressions, open chest cardiac massage and defibrillation (step ABC, i.e. Airway, Breathing and Circulation) was established in the 1960's. This CPR protocol has not taken vulnerability of central nervous system (CNS) into account. Therefore, the key obstacle for current resuscitation is the acutely limited time window, and the major reason for the limited time window is that the CNS is extremely vulnerable to hypoxic-ischemic insult. Traditionally, it is believed that the maximum tolerant survival time for brain in a cardiac arrest patient is about 5 to 8 minutes. Therefore, in clinic, the real problem in circulatory arrest is usually not to restore cardiopulmonary function but instead to prevent brain death.

Shock results in low blood perfusion throughout body. Although the blood perfusion is not completely stopped, shock shares many similar pathological processes with cardiac arrest, and is also a life-threatening condition. Shock can be categorized into anaphylactic, septic, cardiogenic, hypovolemic shock depending on the causes.

The CNS including brain and spinal cord is extremely susceptible to hypoxic-ischemic insults compared with peripheral organ systems such as the liver, kidney, lung, or intestines. The mechanism underlying this susceptibility has not been completely understood. Lacking of an effective approach to protect brain and spinal cord is the ultimate reason why the time window for resuscitation is so limited.

In peripheral tissues, capillaries are relatively permeable and as a result the interstitial fluid (ISF) contains about 2 g/dl of plasma proteins. It is believed that interstitial proteins and hyaluronic acids form a dense network of proteoglycan filaments so that the ISF moves molecule by molecule from one place to another by kinetic motion among proteoglycan filaments in the interstitium. Normally the amount of free-flowing fluid, present in the interstitium is small. A low interstitial protein concentration results in an increased amount of free ISF. An elevated concentration of interstitial protein may reduce the free ISF, but it also attracts more fluid, resulting in increased volume. The lymphatic system is the scavenging pathway for interstitial proteins. By regulating the removal of excess protein, the lymphatic system keeps the interstitial protein concentration around 2 g/dl. This ensures limited free fluid and also regulates the ISF volume. Lymph flow reduces ISF volume resulting in negative interstitial pressure. Therefore, the movement of proteins from plasma to ISF and finally to lymph is important for maintaining extracellular homeostasis.

The CNS lacks a lymphatic system; instead it is bathed by the cerebrospinal fluid (CSF). The CSF is very different from the lymph in peripheral tissues in at least two aspects: protein concentration and the resultant interstitial fluid pressure. The CSF is secreted by the choroid plexuses that line the cerebral ventricles. Tight junctions linking the adjacent choroidal epithelial cells form the blood-CSF barrier and prevent most large molecules from passing into the CSF from the blood. Therefore the CSF contains an extremely low protein concentration. In a human adult, the CSF occupies about 10 percent of the intra-cranial and intra-spinal volume. The average rate of CSF formation is about 21 to 22 ml/hr, or approximately 500 ml/day. The CSF formation is related to intracranial pressure (ICP). When the intracranial pressure is below about 70 mm $H_2O$, the CSF is not absorbed, and production increases. Many agents are known as CSF production inhibitors such as Furosemide and Acetazolamide. The choroid plexuses may not be the only sites for CSF production. Milhorat reported that in monkeys with choroid plexuses removed, up to 60% of the CSF is produced from ISF flow out of the brain. The blood-brain barrier (BBB) prevents proteins from entering the interstitium. Therefore, it is speculated that the ISF in brain, just like the CSF, has a low protein concentration. Importantly, the CSF is contiguous with the ISF, with the Virchow-Robin spaces, serving as a conduit. It is estimated that intracellular protein concentration averages about 16 g/dl in mammalian cells. Therefore water and $Na^+$ in the ISF tend to move easily into cells. To make matters worse, the ICP averages about 10 mmHg leading to a positive interstitial fluid pressure. Taken together, these factors make the CNS prone to edema formation. As a result cells in the CNS constantly consume more energy to remove excess intracellular fluid in physiological condition. When cell energy is compromised, such as in ischemia following cardiac arrest, cells rapidly become swollen, i.e. cytotoxic edema.

Swelling of cerebral tissue can compress blood vessels inside the Virchow-Robin space leading to a persistent deficit in blood perfusion even after the restoration of blood perfusion, termed a 'no-reflow' or 'low reflow' phenomenon. This blood perfusion deficit blocks collateral circulation and induces a feedback loop contributing irreversible cerebral cell death and tissue necrosis.

The treatment disclosed in this invention to protect bran and spinal cord is based on the following measures: (1) reducing interstitial pressure in the CNS, and (2) increasing the concentration of water and ion-binding Polypeptides in the CSF.

Lowering the ICP reduces the interstitial pressure of CNS. For example, the CSF drainage to lower the ICP has been used to prevent spinal cord damage caused by cross-clamping aorta during aortic surgery for more than 50 years. Although it is beneficial in most of the cases, the clinical outcomes of this approach, have been inconsistent. This inconsistent result is likely caused by the CSF remained in the folds and chambers of the CNS after general CSF removal. The brain and spinal cord have complex contours with many sulci, gyri and pools. These complicated structures make it impossible to remove the CSF completely even when ICP is reduced to 0 mmHg. Moreover, surface tension and capillary forces retain CSF in the Virchow-Robin space and in the spaces between the dura and brain surface. This invention addresses problem of treating the remaining CSF after general CSF removal.

Researchers have suggested that bolus infusion of hyperoncotic solution into the cerebral vasculature or perfusion of hyperoncotic artificial CSF can alleviate cerebral edema. The term "hyperonconic" refers to high colloid osmotic pressure caused by the existence of large molecular weight substances that do not pass readily across capillary walls. For example, U.S. Pat. No. 6,500,809 to Frazer Glenn discloses a method of treating neural tissue edema using hyperoncotic artificial CSF. Several colloid osmotic agents including albumin and dextran were used in the method.

This invention, however, reveals that the colloid osmotic pressure is not a key factor. Although albumin is effective in protecting the CNS tissue, it appears that its colloid osmotic effect is not the primary reason for its neural protective effect, because other colloid osmotic agents such as Dextran and Hetastarch are ineffective. In contrast, gelatins, even with molecular weights smaller than cut-off size for colloid osmotic agents are effective. In fact, gelatins with various molecular weights ranging from 20,000 to 100,000 Daltons are all effective regardless of their molecular weights. Collagen and Sericin peptides are also effective. Albumin, gelatin, collagen, and Sericin peptides all belong to poly amino acids category. It is thus the water and ions binding properties of proteins or other polyaminoacids that really matter.

The CNS can be made as resistant to various insults as other organ systems, or at least less vulnerable to such insults, by mimicking lymphatic system of other organs. The present invention is also directed at other mechanisms of ischemic injury that are common to all organ systems, including the use of insulin, magnesium and ATP.

The CSF contains about one fifteenth of plasma insulin concentration (CSF: 0-4 μU/ml; fasting plasma: 20-30 μU/ml). Insulin has also been regarded as a growth factor, evidences have repeatedly proven that insulin yield protection for ischemic cerebral tissue independent of its glucose lowering effect. Compared with other growth factors, insulin has been used in clinic for years, and is much less expensive.

Magnesium ($Mg^{2+}$) is the second highest electrolyte intracellularly (58 mEq/L). ATP (Adenosine 5'-triphosphate) is always present as a magnesium: ATP complex. $Mg^{2+}$ basically provides stability to ATP. At least more than 260 to 300 enzymes have been found to require $Mg^{2+}$ for activation. Best known among these are the enzymes involved in phosphorylations and dephosphorylations: ATPases. phosphatases, and kinases for glycolytic pathway and krebs cycles. At the level of the cell membrane $Mg^{2+}$ is needed for cytoskeletal integrity, the insertion of protein into membranes, the maintenance of bilayer fluidity, binding of intracellular messengers to the membrane, regulation of intracellular $Ca^{2+}$ release by inositol triphosphate etc. $Mg^{2+}$ also affects the activities of pumps and channels regulating ion traffic across the cell membrane. The potential changes in tissue $Mg^{2+}$ might also affect the tissue ATP levels. In tissue culture and animal models elevated $Mg^{2+}$ concentration has been repeatedly proven to protect neurons and other cells.

The concentration of ATP inside cells is high, whereas the concentration outside cells is very low. Harkness and coworkers showed that the ATP concentrations is about 1 to 20 μmol/l in plasma, however in CSF, ATP could not be detected, and it was estimated to be about less than 0.05 μmol/l. Mufioz and coworkers detected that the ATP concentration in CSF is about 16 nM/l. Exogenous ATP provides direct energy to the damaged tissue. Sakama and coworkers showed that continuous application of ATP (100 μM) significantly increased axonal transport of membrane-bound organelles in anterograde and retrograde directions in cultured neurons. Uridine 5'-triphosphate produced an effect similar to ATP. Mg-ATP has been used clinically in Japan to treat hepatic and kidney hypoxia-ischemia.

Acidosis is a universal response of tissue to ischemia. In the brain, severe acidosis has been linked to worsening of cerebral infarction. Recent evidence however suggests that mild extracellular acidosis protects the brain. It has been reported mild acidosis provide cell protection down to pH 6.2. The acidosis that accompanies ischemia is an important endogenous protective mechanism. Correction of acidosis seems to trigger the injury. It has also been speculated that mild acidosis might stimulate anaerobic glycolysis that might supplement NADH oxidation and ATP yields.

DETAILED DESCRIPTION OF AN ILLUSTRATIVE EMBODIMENT

The presence of CSF and ICP are detrimental to ischemic CNS tissue, therefore, removing the CSF or replacing it with lymph-like fluid and reducing the ICP can increase the tolerance of the CNS tissue to ischemia. The main embodiment of this invention is a novel protocol for cardiac arrest resuscitation, named N-CPR, meaning neuro-cardiopulmonary resuscitation.

The N-CPR protocol comprises of three steps. Step 1, injecting Acetazolamide or Furosemide to reduce CSF production. Step 2, removing the CSF, then injecting a invented lymph-like fluid into subarachnoid space, and followed by step 3, conventional CPR (ventilation, cardiac massage). Cardiac arrest results in low ICP, so it is a good opportunity to remove the CSF. Therefore it is preferred that CSF removal starts before cardiac massage as the resumption of heart beat will lead to increased ICP making the CSF removal much more difficult later. When treating a cardiac arrest patient, injecting Furosemide (40-2000 mg) or Acetazolamide (250-1000 mg) intramuscularly or intravenously in an amount effective to reduce or stop the CSF production. The CSF can be removed from lumbar subarachnoid space through lumbar puncture. In addition to lumbar subarachnoid space, the CSF can also be removed from cisterna magna and lateral cerebral ventricles. Optionally, a small hole can be drilled on the skull above each cerebral hemisphere, and the dura is punctured. The CSF can be removed through one or all puncture points. To facilitate CSF removal, two additional procedures can be used. First, when withdrawing CSF from one puncture point, the other puncture point(s) may be kept open. Second, using gravity to dump the CSF to the withdrawing point, for example, with withdrawing CSF from lumbar subarachnoid space, the patient may be kept in a sit position.

Although the CSF removal alone is effective to prolong the time widow for resuscitation, it might not be able to reach the maximum protection. The contour of the CNS is very complex with many sulci, and gyri, therefore, simple CSF removal might inevitably leave part of the tissue unprotected, this can lead to localized tissue damages despite of successful general resuscitation. Therefore, invented lymph-like fluid is injected to replace the CSF, particularly the CSF left in subarachnoid space after the CSF removal.

Another embodiment of the present invention introduces the lymph-like fluid composition for replacing the CSF during cardiac arrest resuscitation. The example components of the lymph-like fluid include (1) Molecules primarily consisting of chemically-linked amino acids, (2) ionic magnesium ($Mg^{2+}$), (3) adenosine triphosphate (ATP), and (4) insulin.

The Polypeptides

Acting as his own lexicographer, the patentee calls the molecules that mainly consist of chemically-linked amino acids as "the Polypeptides" for the sake of simplicity. The Polypeptides have significant water and ions binding capacity. They include a wide variety of molecules, from small peptides containing two or more amino acids to proteins of large molecular weight and multiple peptide chains. The Polypeptides can be natural or synthetic molecules. They also include molecules that consist of amino acids and other building blocks such as hyaluronic acid or glucose (e.g., proteoglycan). The polypeptides are used here to simulate the function of intestinal proteins.

Whether the Polypeptides can pass through the capillary walls to generate colloid osmotic pressure are not important in this invention. In fact, colloid osmotic agents without the Polypeptides, such as Dextran, do not confer neuroprotective effect. It is preferred that the Polypeptides do not readily pass through cell membrane. Therefore, the invention prefers, but is not limited to, Polypeptides with molecular weight between 1,000 to 30,000 Daltons.

Several examples the Polypeptides are described here, including albumin, collagen, gelatin and sericin. Albumin is blood protein and an expensive option for the treatment, considering the current cost of albumin use already accounts for 10 to 30% of pharmacy budgets in hospital units.

Gelatins, on the other hand, can be a much cheaper option for the Polypeptides. Injectable gelatin polypeptides are much cheaper than albumin, and has been used in clinic in many countries such as Europe, China and South Africa. Examples of available commercial pharmaceutical gelatins include GELOFUSINE® and HAEMACCEL®. Sericin and Fibroin, the constituents from the silkworm cocoon, can also be a cheaper option for polypeptides. Examples of available commercial Sericin products are from Silk Biochemical Co Ltd (46-3-108, Zhao hui Yi Qu, Hangzhou, China), and Sinosilk Co Ltd (1 Jincheng Road, Wuxi, Jiangsu China). Various Silk peptides with molecular weight ranging from 300-100,000 can be obtained and be used as polypeptides. Heat shock protein can also be used as the Polypeptide. Example concentrations of the Polypeptides are ranged from 0.1-30 gram/dl. The preferred concentration range is between 1 and 10 gram per dl.

Insulin, ATP, and Other Constituents

The insulin concentration should be in a range from 0.01 to 1000 µU/ml. The preferred insulin concentration is between 1 and 60 µU/ml. All growth factors having insulin-like effect can be chosen to replace insulin. For examples, insulin-like growth factors, nerve growth factor, brain derived neurotrophic factor, neurotrophin, fibroblast growth factor and glial cell line derived neurotrophic factor, erythroproietin, growth hormone, and growth hormone releasing factor may be used to replace insulin or may be used in combination with insulin.

The ATP concentration should be in a range from 16 nM to 5 mM. The preferred ATP concentration is between 0.001 to 1 mM. The most preferred ATP concentration is between 0.001 and 0.01 mM. Other high energy compound such as Uridine 5'-triphosphate can be used to replace ATP.

The components and concentration range of the $Mg^{2+}$ and artificial CSF can be as follow: Na 120-155 meq/L, K 0.1-5.0 meq/L, Ca 0.1-3.0 meq/L, P 0.1-2 meq/L, Cl 120-155 meq/L, Mg 0.4-8 meq/L, $HCO_3$ 0-25 meq/L, Glucose 0-60 mg/dl and water. The preferred concentration range of the $Mg^{2+}$ and artificial CSF is as follow: Na 150 meq/L, K 3.0 meq/L, Ca 1.4 meq/L, P 1.0 meq/L, Cl 155 meq/L, Mg 2.5-5 meq/L, and water.

Normal blood pH value is about 7.35 to 7.45. The pH value of the composition should be in a range between 6.2 to 7.45. The pH value between 6.8-7.0 is preferred. The final osmolality of the lymph-like fluid should be between 280-340 mOsm/L.

To make the lymph-like fluid, molecules consisting of the Polypeptides, insulin, ATP and artificial CSF may be manufactured in a ready to use condition. Optionally, artificial CSF with elevated $Mg^{2+}$ concentration may be manufactured in one container, the mixture of molecules consisting of the Polypeptides, insulin and ATP may be assembled in another container.

The lymph-like fluid composition may also contain other nutrients such as vitamins (e.g., D-Calcium Pantothenate, Choline, Folic acid, i-Inositol, Niacinamide, Pyridoxal, Riboflavin, Thiamine, Vitamin $B_{12}$ etc.), Amino acids (e.g., L-Alanine, L-Arginine, L-Asparagine, L-Cysteine, L-glutamine, L-glutamate, Glycine, L-Histidine, L-Isoleucine, L-leucine, L-lysine, L-methionine, L-Phenylalanine, L-proline, L-serine, L-threonine, L-tryptophan, L-tyrosine, L-valine etc.), phospholipids, Cholesterol, fat, fatty acid, D,-L-alpha-tocopherol, antioxidant etc.

The lymph-like or a plasma-like fluid composition may also contain oxygen carriers such as bis-perfluorobutyl ethylene (oxygenated before use), intermediate molecules of glycolysis (e.g., fructose-1,6-biphophate, glyceraldehyde-3-phosphate, 1,3 bisphosphoglycerate, 3-phosphoglycerate, 2-phosphoglycerateare, phosphoenolpyruvate, pyruvate), enzymes for glycolysis (e.g., hexokinase, phosphoglucose isomerase, phosphofructokinase, aldolase, triosephosphate isomerase, glyceraldehydes 3-phosphate dehydrogenase, phosphoglygerate kinase, pyruvate kinase etc.), fructose-2,6-biphosphate, and intermediates of Krebs cycle.

The lymph-like or a plasma-like fluid compositions herein may also be advantageously combined with any of the agents used to treat stroke or other neurological deficiencies based on other mechanisms including: calcium channel blockers such as Nimodipine and Flunarizine; calcium chelators such as DP-b99, potassium channel blockers, Free radical scavengers (e.g., antioxidants such as Ebselen, porphyrin catalytic antioxidant manganese (III) meso-tetrakis (N-ethylpyridinium-2-yl) porphyrin, (MnTE-2-PyP (5+)), disodium 4-[(tert-butylimino)methyl]benzene-1,3-disulfonate N-oxide (NXY-059), N:-t-butyl-phenylnitrone or Tirilazad), GABA agonists including Clomethiazole, GABA receptor antagonists, glutamate antagonists (e.g., AMPA antagonists such as GYKI 52466, NBQX, YM90K, YN872, ZK-200775 MPQX, Kainate antagonist SYM 2081, NMDA antagonists such as CGS 19755, NMDA channel blockers including Aptiganel (Cerestat) and CP-101,606, Dextrorphan, destromethorphan, magnesium, metamine, MK-801, NPS 1506, and Remacemide), glycine site antagonists including ACEA 1021 and GV 150026, polyamine site antagonists such as Eliprodil, and Ifenprodil, adenosine receptor antagonists, Nitric oxide inhibitors including Lubeluzole, opiod antagonists such as Naloxone and Nalmefenem, Phosphatidylcholine precursor, Citicoline (CDP-coline), serotonin agonists including Bay x 3072, Sodium channel blockers (e.g., Fosphenytoin, Lubeluzole, and 619C89), potassium channel openers such as BMS-204352, anti-inflamatory agents, protein kinase inhibitors, and other active agents that provide energy to cells such as co-enzyme A, co-enzyme Q, or cytochrome C. Similarly, agents known to reduce cellular demand for energy, such as phenytoin, barbital, or lithium may also be added. These agents may be added into this lymph-like composition or may be administered orally or intravenously in combination with this invented composition and method.

The aim of introducing the invented lymph-like fluid composition is to treat any remaining CSF following general manual CSF removal. By introducing the lymph-like fluid composition into the subarachnoid space around injured CNS, the remaining CSF of the inaccessible spaces will be diluted and finally replaced by the lymph-like fluid composition. After removal of the CSF, the lymph-like fluid composition will be injected into the subarachnoid space through the puncture point where the CSF was removed. The injected lymph-like composition is approximately equal or less to the amount of CSF removed. The injected lymph-like fluid composition may be withdrawn then injected back repeatedly for several times to 'wash' the CNS tissue. This 'wash' procedure may be performed through one or more puncture points, injecting at one point while withdrawing at other point(s). The 'wash' procedure may take from one minute to a few ten minutes, or may take hours in complicated case. The lymph-like fluid composition may or may not be re-used for the 'wash' procedure. Finally, a mount of the lymph-like composition will be removed to reduce the ICP after the 'wash' procedure, and the ICP may be maintained at range between 0 and 15 mm Hg with lymph-like fluid composition. The lower the ICP is, the better the outcome. It is preferred that the final ICP is maintained at 0-7 mm Hg. The CSF in sulci, gyri, pools, and the Virchow-Robin space is diluted and replaced by the lymph-like fluid composition nourishing the injured CNS. The 'wash' procedure can be repeated every 3-4 hours or as needed. Optionally, the lymph-like fluid composition may be replaced by blood plasma or serum during the 'wash' procedure. Alternatively, patient's own CSF may be used to replace artificial CSF in the lymph-like fluid composition. Usually 50-200 ml of the patient's own CSF can be obtained as a solvent to dissolve the mixture of polypeptides, insulin, $Mg^{2+}$ and ATP. Elliot B solution is an artificial CSF that has been approved as a solvent since 1996 in USA. Elliot B solution may also be used to replace artificial CSF.

In addition to 'wash' the CNS directly through subarachnoid space, the lymph-like fluid composition can also be infused through blood circulation. Because of smaller molecular weight, the polypeptides and other nutrients of the lymph-like fluid composition can pass through the blood brain barrier and blood CSF barrier to enter the interstitium of cerebral tissue and the CSF. Therefore infusing the invented lymph-like fluid composition into blood stream will enhance neuroprotective efficacy. In addition, cardiac arrest results in whole body ischemia, the lymph-like fluid composition into blood stream can easily enter the interstitium of all peripheral organ systems making them more tolerant to ischemia.

EXAMPLE ONE

Making of the Lymph-like Fluid Composition

Artificial CSF was made according to table 1.

TABLE 1

| Component | Amount |
| --- | --- |
| NaCl | 8.182 gram |
| KCl | 0.224 gram |

TABLE 1-continued

| Component | Amount |
| --- | --- |
| $CaCl_2 \cdot 2H_2O$ | 0.206 gram |
| $Na_2HPO_4$ | 0.113 gram |
| $NaH_2PO_4$ | 0.023 gram |
| $MgSO_4$ | 0.361 gram |

Sterile water for dilution to 1000 ml

Mixture of Sericin peptide (molecular weight 2500-6000 Daltons), Insulin and ATP were made according to table 2.

TABLE 2

| Sericin peptide | 40 grams |
| --- | --- |
| Insulin | 3,000 µU |
| ATP | 0.55 milligrams |

Mix these substances in one container

Dissolve the mixture of Sericin peptide, Insulin and ATP in artificial CSF. Final pH of the composition was adjusted to between 6.8 to 7.0.

EXAMPLE TWO

Making of the Lymph-like Fluid Composition

Artificial CSF was made according to table 1 in example one.

Mixture of Gelatin (molecular weight between 20,000-25,000 Daltons), Insulin and ATP were made according to table 3.

TABLE 3

| Gelatin | 35 grams |
| --- | --- |
| Insulin | 3,000 µU |
| ATP | 0.55 milligrams |

Mix these substances in one container

Dissolve the mixture of Gelatin, Insulin and ATP in artificial CSF. Final pH of the composition was adjusted between to 6.8 to 7.0.

EXAMPLE THREE

N-CPR Procedure for Cardiac Arrest 24 rats weighing between 250-300 grams were divided into four groups. 5% Isoflorane was given for anesthetic induction. All animals underwent placement of a saline filled right femoral artery and right femoral vein catheter for monitoring mean blood pressure (MBP) and for drug administration. Following tracheostomy and endotracheal intubation, all animals were mechanically ventilated with 1% isoflorane, 70% nitrous oxide in oxygen at a rate of 50 breaths/minute with tidal volume of 12 ml/kg. A silicone catheter (0.025 OD, 0.012 ID inch) was surgically implanted in the cisterna magna as a draining route. A hole of 3 mm in diameter was drilled on the skull above each cerebral hemisphere (3 mm lateral to midline and 3 mm in front of the bregma), dura was punctured, an infusing silicone catheter (0.025 OD, 0.012 ID inch) was placed and fixed with glue in the hole into the subarachnoid spaces on the surface of each cerebral hemisphere.

The cardiac arrest was induced by electrical stimulation (alternating current: 12 V, 50 Hz) via the esophageal electrode and an external electrode covered with electrode gel and placed on the animals chest. Ventilation was stopped. Complete circulatory arrest was indicated by an abrupt decrease in MAP below 15 mm Hg. The cardiac arrest was lasted for 10 minutes.

For group one (n=6): Conventional CPR. At 10 minutes after cardiac arrest, 0.2 mg/kg epinephrine and 0.5 mmol/kg bicarbonate ($NaHCO_3$) were administered through femoral vein catheter. Simultaneously, animal were ventilated with 100% oxygen at prearrest tidal volume and respiration rate. Cardiac massage started at 10 seconds after ventilation to allow the lungs to stretch. Cardiac massage was performed by manual closed chest compression at rate of 200/minute, with two fingers compressing the chest to maximize MAP.

For group two (n=6): Removing the CSF plus conventional CPR. At 10 minutes after cardiac arrest, first administering 20 mg Furosemide through femoral vein catheter, then the CSF was removed as completely as possible from catheter in cisterna magna and from catheters above each cerebral hemisphere. The CSF removal took about 1 minute. Immediately after the CSF removal, conventional CPR was performed as described in group one.

For group three (n=6): Removing the CSF and replacing it with invented lymph-like fluid composition (made according to example one) plus conventional CPR. At 10 minutes after cardiac arrest, first administering 20 mg Furosemide through femoral vein catheter, then the CSF was removed as completely as possible from catheter in cisterna magna and from catheters above each cerebral hemisphere. The CSF removal took about 1 minute. Immediately after the CSF removal, 1 ml of lymph-like fluid composition (made according to example one) was quickly flushed in from catheters above each cerebral hemisphere and flushed out from catheter in cisterna magna. The flushing took about 1 minute. Immediately after flushing, conventional CPR was performed as described in group one, simultaneously, 3 ml of the lymph-like fluid composition (made according to example one) was continuously infused from catheters above each cerebral hemisphere and was drained out from the catheter in cisterna magna. The infusion lasted for 3 hours at a rate of 1 ml/hour and the ICP was maintained at 0-10 mmHg.

For group four (n=6): Removing the CSF and replacing it with invented lymph-like fluid composition (made according to example two) plus conventional CPR. At 10 minutes after cardiac arrest, first administering 20 mg Furosemide through femoral vein catheter, then the CSF was removed as completely as possible from catheter in cisterna magna and from catheters above each cerebral hemisphere. The CSF removal took about 1 minute. Immediately after the CSF removal, 2 ml of lymph-like fluid composition (made according to example two) was quickly flushed in from catheters above each cerebral hemisphere and flushed out from catheter in cisterna magna. Then the lymph-like fluid composition was removed from subarachnoid space. The flushing and removing of composition took about 2 minute. Immediately after flushing and removing, conventional CPR was performed as described in group one. The ICP was maintained at 0 mm Hg.

At 24 hours, all rats were tested for behavioral deficit by the following criteria: Maximum Score=400 (meaning brain death or death); Minimum Score=0 (meaning normal brain function).

1. Level of Consciousness
    0=complete awareness of auditory stimuli.
    30=clouded: apparently conscious but drowsy or intermittently irritable on clapping hands and pinching nailbeds of hindlegs.
    60=stupor: response with movements to pinching nailbed of hindlimb, open eyes, movements may be either purposeful or reflex.
    100=coma: no movement on painful stimulation (pinching nailbed of hindlimb; should be confirmed on forelimbs as well).

2. Respiratory Pattern
    0=normal rate and rhythm.
    50=abnormal spontaneous breathing (e.g., periodic gasps, irregular rhythm)
    75=breathing, but not enough to maintain normal arterial blood gases.
    100=apnea: complete absence of spontaneous respiratory efforts 3. Cranial Nerve Function
    Pupil size: examine in room lighting and record diameters of pupil and iris (R/L)
        0=normal: 1-2 mm diameter
        10=abnormal: greater than 3 mm
        20=severely abnormal: greater than 5 mm, pinpoint, or new anisocoria
    Papillary response to light: use flashlight (R/L)
        0=normal
        10=sluggish
        20=absent
    Eyelid reflex:
        0=normal
        10=sluggish
        20=absent
    Corneal reflex: Test with moist cotton swab, observe for eyelid closure (R/L)
        0=normal
        10=sluggish
        20=absent
    Swallow reflex:
        0=normal
        10=sluggish
        20=absent 4. Motor and Sensory Function
    Motor response to painful stimulus: Pinch each limb, observe for withdrawal response.
        0=normal
        25=no response
        50=coma (no test required)
    Positioning: place rat in left lateral decubitus position and observe position assumed.
        0=normal
        25=mildly abnormal or perceptible movement, or intermittent running movements
        50=markedly abnormal, no any movement.

The results are as follow:

In group one, four rats were not able to survive for 24 hours. Scores in other two rats are 400 and 360 respectively.

In group two, the scores are 100, 120, 100, 140, 80 and 150 respectively.

In group three, the scores are 80, 60, 60, 80, 60 and 40 respectively.

In group four, the scores are 80, 70, 60, 100, 40 and 60 respectively.

It is concluded that N-CPR procedure is effective in resuscitating cardiac arrest.

While my above description contains many specifics, these should not be construed as limitations on the scope of the invention, but rather as illustrative examples.

The invention claimed is:

1. A method for resuscitating cardiac arrest in a mammal, comprising the following two steps in either order:
   removing a cerebrospinal fluid (CSF) from a subarachnoid space in central nervous system, and
   applying a conventional cardiopulmonary resuscitation (CPR) procedure including open airway, breathing, and circulation.

2. A method for resuscitating cardiac arrest in a mammal, comprising the following two steps in either order:
   infusing an amount of a lymph-like fluid composition into a subarachnoid space effective to replace a cerebrospinal fluid (CSF), wherein the lymph-like fluid composition comprises an artificial cerebrospinal fluid comprising 120-155 meq/L of Na, 0.1-5.0 meq/L of K, 0.1-3.0 meq/L of Ca, 0.1-10 meq/L of P, 120-155 meq/L 0.9-8 meq/L of Mg, and water, and at least one component selected from the group consisting of 0.1-30 gram/dl of polypeptides, 1 to 60 μU/ml of insulin, and 0.001 to 0.05 mM of ATP, and
   applying a conventional cardiopulmonary resuscitation (CPR) procedure including open airway, breathing, and circulation.

3. A method for resuscitating cardiac arrest in a mammal, comprising the following two steps in either order:
   removing an amount of a cerebrospinal fluid (CSF) from a subarachnoid space in central nervous system and followed by repeatedly injecting and withdrawing an effective amount of a lymph-like fluid composition through the subarachnoid space to wash the central nervous system tissue, and finally removing an amount of the lymph-like fluid composition effective to reduce the intracranial pressure (ICP); wherein the lymph-like fluid composition comprises an artificial cerebrospinal fluid comprising 120-155 meq/L of Na, 0.1-5.0 meq/L of K, 0.1-3.0 meq/L of Ca, 0.1-10 meq/L of P, 120-155 meq/L 0.9-8 meq/L of Mg, and water, and at least one component selected from the group consisting of 0.1-30 gram/dl of polypeptides, 1 to 60 μU/ml of insulin and 0.001 to 0.05 mM of ATP,
   cardiopulmonary resuscitation (CPR) procedure including open airway, breathing, and circulation.

4. A method for resuscitating cardiac arrest in a mammal according to claim 2, further comprising injecting a volume of the lymph-like fluid composition into blood stream.

5. A method for resuscitating cardiac arrest in a mammal according to claim 3, further comprising injecting a volume of the lymph-like fluid composition into blood stream.

6. A method for resuscitating cardiac arrest in a mammal according to in claim 1, wherein removing the CSF from the subarachnoid space is performed from at least one point selected from lumbar, cisterna magna, lateral ventricle, or skull above each cerebral hemisphere.

7. A method for resuscitating cardiac arrest in a mammal according to claim 1, wherein the mammal is in a sit position when removing the CSF.

8. A method for resuscitating cardiac arrest in a mammal according to claim 2, wherein infusing the lymph-like fluid composition is performed from at least one point selected from the lumbar, cisterna magna, lateral ventricle, or skull above each cerebral hemisphere.

9. A method for resuscitating cardiac arrest in a mammal according to claim 3, wherein removing the CSF and injecting and withdrawing the lymph-like fluid composition are performed from at least one point selected from lumbar, cisterna magna, lateral ventricle, or skull above each cerebral hemisphere.

10. A method for resuscitating cardiac arrest in a mammal according to claim 2, wherein the mammal is in a sit position when infusing the lymph-like fluid composition.

11. A method for resuscitating cardiac arrest in a mammal according to claim 3, wherein the mammal is in a sit position when removing the CSF and injecting and withdrawing the lymph-like fluid composition.

12. A method for resuscitating cardiac arrest in a mammal according to claim 1, wherein the intracranial pressure (ICP) is maintained at 0-10 mmHg after removing the CSF from the subarachnoid space.

13. A method for resuscitating cardiac arrest in a mammal according to claim 2, wherein the intracranial pressure (ICP) is maintained at 0-10 mmHg with the lymph-like fluid composition.

14. A method for resuscitating cardiac arrest in a mammal according to claim 3, wherein the intracranial pressure (ICP) is maintained at 0-10 mmHg with the lymph-like fluid composition.

15. A method for resuscitating cardiac arrest in a mammal according to claim 2, wherein the lymph-like fluid composition comprises Gelatin.

16. A method for resuscitating cardiac arrest in a mammal according to claim 2, wherein the lymph-like fluid composition comprises Albumin.

17. A method for resuscitating cardiac arrest in a mammal according to claim 3, wherein the lymph-like fluid composition comprises Gelatin.

18. A method for resuscitating cardiac arrest in a mammal according to claim 3, wherein the lymph-like fluid composition comprises Albumin.

* * * * *